United States Patent [19]
Eberhardt

[11] Patent Number: 5,279,612
[45] Date of Patent: Jan. 18, 1994

[54] DYNAMIC FIXATION OF PORCINE AORTIC VALVES

[75] Inventor: Carol E. Eberhardt, Fullerton, Calif.

[73] Assignee: Medtronic, Inc., Minneapolis, Minn.

[21] Appl. No.: 741,215

[22] Filed: Aug. 2, 1991

Related U.S. Application Data

[63] Continuation of Ser. No. 366,375, Jun. 9, 1989, abandoned.

[51] Int. Cl.$^5$ .................................................. A61F 1/22
[52] U.S. Cl. ................................. 8/94.11; 623/2; 623/3
[58] Field of Search .................. 623/2, 3; 8/94.11

[56] References Cited

U.S. PATENT DOCUMENTS 3,966,401  6/1976  Hancock .......................... 8/94.11
4,372,743  2/1983  Lane ................................ 8/94.11

Primary Examiner—Jacqueline V. Howard
Attorney, Agent, or Firm—Reed A. Duthler; Harold R. Patton

[57] ABSTRACT

A method of preserving porcine heart valves so that they may be incorporated into prosthetic heart valves for human implant. During fixation, the leaflets of the valves are repeatedly flexed throughout their full range of motion. Flexing of the leaflets continues throughout fixation, and is accomplished by providing for alternating fluid flow through the valve from the inflow and outflow sides sufficient to cause the leaflets to fully open and close.

17 Claims, 2 Drawing Sheets

DYNAMIC FIXATION OF PORCINE AORTIC VALVES

This is a continuation of application Ser. No. 07/366,375, filed Jun. 9, 1989, now abandoned.

BACKGROUND OF THE INVENTION

This invention relates generally to prosthetic heart valves, and more particularly to porcine xenograft heart valves, and their methods of preparation.

Traditionally, porcine heart valves are treated with a cross-linking agent or tanning fluid in order to stabilize the tissue against degradation. There have been a variety of approaches taken, but most involve exposure of the porcine valve to glutaraldehyde or other cross-linking agent, with the valve displaying a configuration in which the leaflets are closed. Maintaining the leaflets in closed position has typically been accomplished by providing a pressure differential across the valve. Pressure differential is used in a range from less than 4 mm Hg, as set forth in U.S. Pat. No. 4,372,743, issued to Lane, up to 120 mm Hg, as disclosed in U.S. Pat. No. 4,050,893, issued to Hancock et al. Fixation has also been accomplished without a pressure differential across the valve, in which case the valve is fixed with leaflets assuming a relaxed, neutral position. One such method is suggested in the article "Influence of Fixation Conditions on the Performance of Glutaraldehyde-Treated Porcine Aortic Valves: Towards a More Scientific Basis", by Broom et al, published in *Thorax*, Vol. 34, pp. 166–176, 1979.

An alternative method of fixing heart valve tissue is set forth in U.S. Pat. No. 3,966,401, issued to Hancock et al. In the method disclosed therein, the outflow side of the heart valve is coupled to a source of pressurized fixative, and the pressure applied to the outflow side of the heart valve is pulsed, from a high pressure level in the range of 80 to 120 mm, down to a low, or in some cases, negative pressure. It is believed that this process would provide a repetitive ballooning and relaxing of the aorta and valve leaflets. However, actual fluid flow through the valve is not disclosed, and it is believed that this process would not result in the repetitive opening and closing of valve leaflets during fixation.

SUMMARY OF THE INVENTION

The fixation method of the present invention allows the leaflets of the valve to be fixed while continually being opened and closed. This is believed to provide a valve of superior flexibility after fixation, and to provide a valve which performs better hemodynamically than the valves of the prior art. Because the leaflets are in motion during fixation, cross-linking due to the fixative does not occur in such a fashion as to interfere with the normal opening and closing movements of the valve. In the preferred method of fixation, flow through the valve is regulated so as to not unduly stress the valve, and allows for preservation of the microstructure of the valve leaflet, and preserving the collagen in its normal "crimped" configuration.

The valve leaflets are opened and closed by inducing an alternating flow of fixative solution through the valve, sufficient to cause full opening and closing of the leaflets. In the preferred embodiments, this is accomplished by moving the valves within a tank of fixative solution, rather than by attaching the valves to a manifold.

DETAILED DESCRIPTION OF THE DRAWINGS

Figure 1:
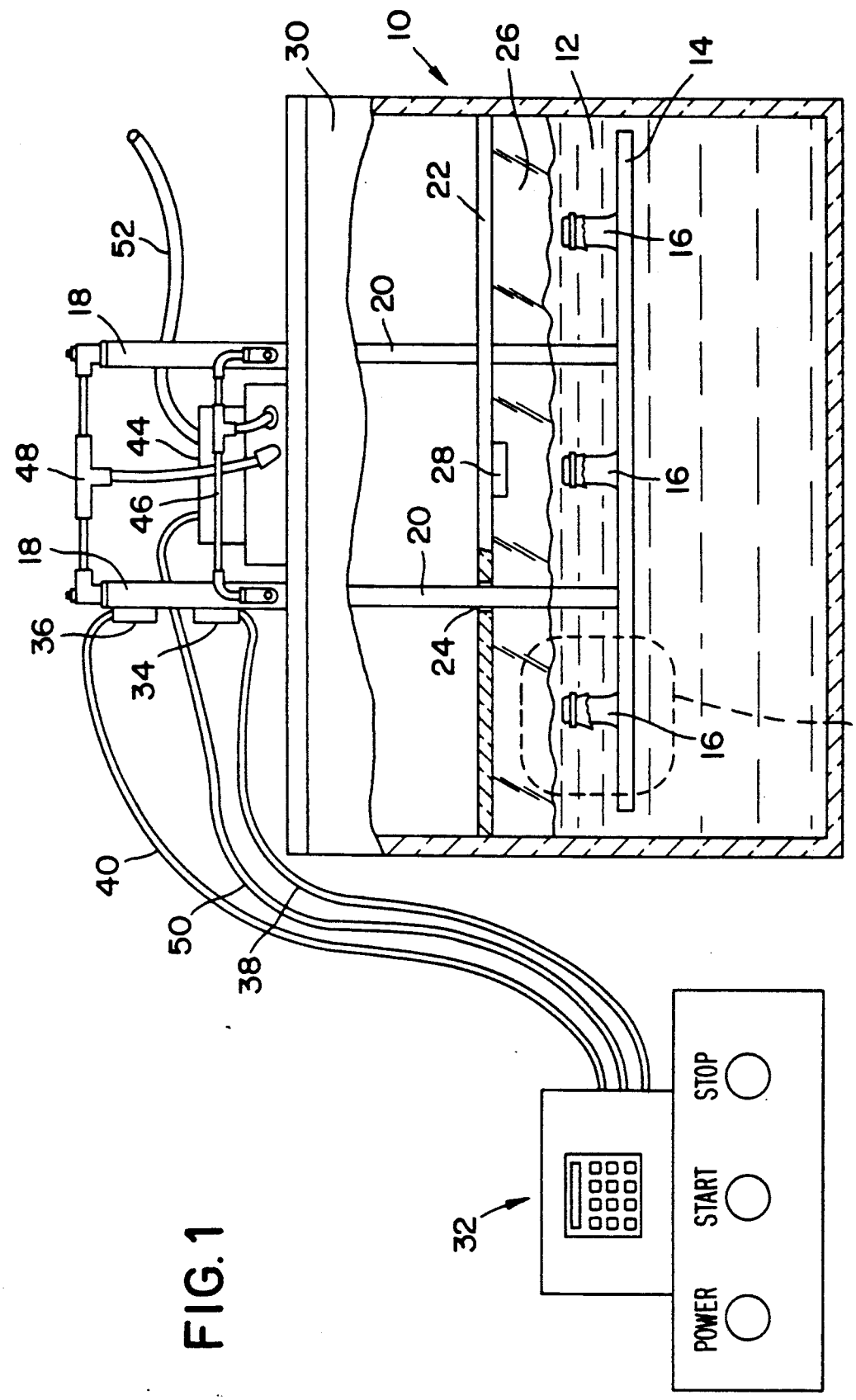
FIG. 1 is side cutaway view of the apparatus used to perform the fixation method of the present invention.

FIG. 1 shows a cutaway view of the fixation tank and associated apparatus used in conjunction with the method according to the present invention. The tank 10 is manufactured of transparent plastic, to allow for observation of the operation of the device, and for monitoring of the valves while in the fixation tank. In use, the tank contains a fixative solution 12. A 0.2 percent gluteraldehyde solution has been found to be appropriate, however, other fixatives such as formaldehyde or other fixative concentrations may also be useful in conjunction with the present method. In some instances, it may be desirable to begin the fixation process in a physiologic saline solution, and gradually introduce the fixative over time until the desired final concentration is achieved.

The fixing apparatus includes a moving plate 14, which has mounting holes for a number of heart valves. As illustrated, plate 14 has mounting locations for nine heart valves 16, organized in three rows of three valves each. Plate 14 is provided with an aperture beneath each of the illustrated heart valves 16, allowing for flow of fixative into the heart valves. As illustrated, the heart valves 16 are mounted still attached to the aorta, with their outflow sides facing downward, toward plate 14. However, apparatus in which the outflow sides of the valves face upward are also believed workable. Plate 14 is moved up and down within tank 10 by means of pneumatic rams 18 which are coupled to plate 14 by means of rods 20.

In order to avoid splashing of the fixative onto rams 18 or out of the tank 10, an intermediate plate 22 is located above the level of fixative 12. Plate 22 is provided with apertures 24, through which rods 20 slide. Plate 22 is supported by the top edge 27 of wall 26. The rear edge of plate 22 is supported by a bracket 28, which is mounted to wall 30, much of which has been cut away in this illustration for the sake of clarity.

In use, plate 14 is repeatedly moved up and down within the tank, allowing heart valves 16 to break through the upper surface of fixative 12 during each upstroke. The valve leaflets open during each upstroke and close during each downstroke.

Oscillation of plate 14 is controlled by control console 32, which is coupled to sensors 34 and 36. Sensors 34 and 36 indicate that rams 18 have reached the bottom and top, respectively of their stroke cycle. Cables 38 and 40 couple sensors 34 and 36 to tank controller 32. At the top and bottom of each stroke, tank controller 32 causes control valve assembly 42 to reverse the direction of the stroke, by switching air flow between manifolds 46 and 48. Control valve assembly 44 is coupled to tank controller 32 by means of cable 50. Compressed air to power pneumatic rams 18 is provided via an air hose 52, which is coupled to a source of compressed air.

Although it is believed that a variety of cycle lengths, stroke times, and fixation periods can be appropriately utilized in conjunction with the present method, the inventors have found that a stroke length of approximately 4", repeated at a frequency of 52 strokes per minute, and continued for a period of at least three days, provides beneficial results. Stroke frequency may be varied, but it is believed that choosing a frequency within the range of normal heart rhythm (e.g. 30–150 strokes/min) appears to be preferable. In order to avoid undue stress to the leaflets, a stroke frequency closer to the lower end of this range (e.g. 30–70 strokes/min) appears desirable. Total fixation cycle time may be regulated by means of a timer or by means of a stroke counter. Valves fixed in this fashion display significant advantages over valves fixed according to prior art methods.

The first gultaraldehyde treated aortic valves were fixed under relatively high pressures up to 120 mm Hg. It has been demonstrated that when aortic leaflets are fixed under pressure, loss of the natural collagen crimp geometry occurs, which significantly effects the opening and closing behavior of the leaflets. More recently, glutaraldehyde treated aortic valves have been fixed using lower pressures, and some have been fixed using no pressure differential whatsoever across the valve leaflets. Valves fixed under any significant closing pressure display loss or elimination of the natural collagen crimp geometry. This permanent alteration of the collagen fibers is believed to result in decreased valve durability. Valves fixed with zero pressure differential across the valve have been shown to retain their natural collagen crimp, yet demonstrate some loss of total orifice area.

Mechanical testing reveals that valves fixed using the dynamic fixation process of the present invention display reduced radial extensibility comparable to a pressure fixed valve, while retaining similar circumferential extensibility to zero pressure fixed tissue. Flow studies indicate that the dynamic fixation process yields a significant improvement in effective orifice area as compared to zero pressure fixed valves. Moreover, durability testing indicates superior in vitro wear characteristics. In summary, valves fixed employing the dynamic fixation process display improved flexibility, retain their natural collagen crimp and display a large total opening area. The use of the dynamic fixation process is therefore believed to provide a valve which represents a substantial advance in the art.

Figure 2:
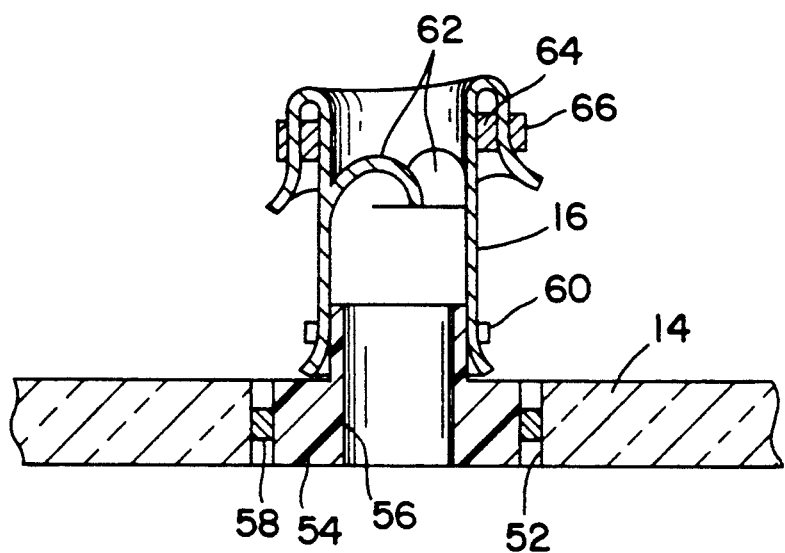
FIG. 2 is a sectional view of a porcine aortic valve mounted to the apparatus illustrated in FIG. 1.

FIG. 2 shows one of the heart valves 16 mounted to plate 14. In this sectional view, it can be seen that plate 14 is provided with an orifice 52, in which a mounting mandrel 54 is located. Mandrel 54 is provided with an internal lumen 56, which communicates with the interior of the aorta to which valve 16 is attached. Mandrel 54 is retained within hole 52 by means of a resilient sealing ring 58. Because plate 14, mandrel 56 and sealing ring 58 will be immersed in fixative, it is preferable that they be fabricated of inert plastics which show good resistance to the highly oxidative environment the fixative provides. The segment of aorta remaining attached to valve 16 is mounted to mandrel 54 by means of tie wrap 60. Preferably, the lower margins of the leaflets of valve 16 are spaced at least 2-3 mm away from mandrel 54.

In practice, it is necessary to keep the tissue attached to the aortic root away from the inflow side of valve 62, to prevent it from entering the valve leaflets and interfering with the fixation process. As such, tissue attached to the inflow side of the valve is mounted between two concentric rings 64 and 66, which serve to keep the inflow side of the valve orifice clear. Because there are no inserts within the valve in the vicinity of the leaflets, the leaflets are free to open and close in their normal fashion.

In the configuration illustrated, the tank and controller are capable of providing a wide range of pressures across the valve, while the valve is closed, on its downstroke. However, it appears desirable to move the valves only fast enough and far enough to insure their complete opening and complete closure, and no faster. As noted above, a 4" stroke running at a rate of approximately 52 beats per minute will provide an appropriate flow through the valve to effect its full opening and closing, without unduly stressing the valve. After fixation, the valves are removed from mandrel 60 and rings 64 and 66. They may then be trimmed and mounted in valve stents or left unmounted and prepared for implant.

The apparatus for accomplishing the method of the present invention is intended to be exemplary, rather than limiting. For example, in the disclosed embodiment, the valves are moved upward through the surface of the fixative solution on their upstroke. However, it is believed that useful results would also be obtained by systems in which the valves remain totally submerged within the fixative.

Similarly, while the disclosed method moves the valves relative to the fixative level, it would be theoretically possible to move the fixative relative to the valves.

In conjunction with the above disclosure, I claim:

1. A method of preserving porcine heart valves, comprising exposing said valves to a fixative solution while repeatedly alternating fluid flow of said fixative solution through said valves in a fashion to cause repeated full opening and closing of said valves due to fluid flow of said fixative.

2. A method according to claim 1 wherein said alternating fluid flow through said valves continues throughout the fixation process.

3. A method according to claim 1 wherein said fixative solution comprises glutaraldehyde.

4. A method according to claim 1 wherein said method comprises mounting said valves to a plate containing a plurality of orifices, each orifice in the plate in fluid communication with one of said valves and wherein said plate is oscillated within said fixative to cause said repeated alternating fluid flow through said valves.

5. A method according to claim 4 wherein said plate is oscillated between a first position in which said valves are completely submerged within said fixative and a second position wherein said valves emerge from said fixative solution.

6. A method according to claim 1 or claim 2 or claim 3 wherein said fixation time continues for a period of at least about three days.

7. A method according to claim 1 or claim 2 or claim 3 wherein the alternating fluid flow causes opening and closing of said valves at a frequency within the range of normal heart rhythm.

8. A heart valve preserved according to the process of claim 1 or 2.

9. A heart valve preserved according to the process of claim 3.

10. A heart valve preserved according to the process of claim 4 or 5.

11. A heart valve preserved according to the process of claim 7.

12. A method according to claim 7 and wherein the fluid flow is alternated at a frequency of about 30 to about 70 cycles per minute.

13. A method according to claim 12 and wherein the fluid flow is alternated at a frequency of about 50 cycles per minute.

14. A method according to claim 5 and wherein the plate is oscillated a distance of about 4 inches in each direction.

15. A heart valve produced according to the process of claim 12.

16. A heart valve produced according to the process of claim 13.

17. A heart valve produced according to the process of claim 14.

* * * * *